(12) United States Patent
Lu et al.

(10) Patent No.: US 7,655,805 B2
(45) Date of Patent: Feb. 2, 2010

(54) METHOD FOR SYNTHESIZING BENZOTRIAZOLE

(75) Inventors: Ling Lu, Taoyuan Hsien (TW);
Po-Hsuan Wei, Taoyuan Hsien (TW);
Chung-Ning Fan, Taoyuan Hsien (TW);
Yu-Cheng Lee, Miaoli Hsien (TW);
Hui-Ling Yang, Pingtung Hsien (TW);
Yu-Chin Lee, Taipei (TW)

(73) Assignee: UFC Corporation (TW)

( * ) Notice: Subject to any disclaimer, the term of this patent is extended or adjusted under 35 U.S.C. 154(b) by 0 days.

(21) Appl. No.: 12/081,983

(22) Filed: Apr. 24, 2008

(65) Prior Publication Data
US 2009/0270632 A1    Oct. 29, 2009

(51) Int. Cl.
*C07D 249/20* (2006.01)
(52) U.S. Cl. .................. 548/260; 548/110; 548/259
(58) Field of Classification Search ............ 548/110, 548/259, 260
See application file for complete search history.

(56) References Cited

U.S. PATENT DOCUMENTS

| 3,715,334 | A | 2/1973 | Kardstet |
| 3,947,436 | A | 3/1976 | Rocktaschel et al. |
| 4,051,161 | A | 9/1977 | Proskow |
| 4,122,233 | A | 10/1978 | Proskow |
| 4,188,451 | A | 2/1980 | Humphrey, Jr. |
| 4,233,430 | A | 11/1980 | Jacquet et al. |
| 4,316,033 | A | 2/1982 | Ching |
| 4,342,742 | A | 8/1982 | Sebag et al. |
| 4,373,060 | A | 2/1983 | Ching |
| 4,457,911 | A | 7/1984 | Conner et al. |
| 4,489,057 | A | 12/1984 | Welters et al. |
| 4,490,356 | A | 12/1984 | Sebag et al. |
| 4,696,969 | A | 9/1987 | Thimineur et al. |
| 4,814,162 | A | 3/1989 | Lang et al. |
| 4,851,587 | A | 7/1989 | Franko-Filipasic et al. |
| 4,859,759 | A | 8/1989 | Maycock et al. |
| 4,868,251 | A | 9/1989 | Reich et al. |
| 5,089,250 | A | 2/1992 | Forestier et al. |
| 5,102,707 | A | 4/1992 | Canivenc et al. |

FOREIGN PATENT DOCUMENTS

| EP | 0138321 | 4/1985 |
| EP | 0354145 | 7/1990 |
| GB | 2077280 A | 12/1981 |

*Primary Examiner*—Patricia L Morris
(74) *Attorney, Agent, or Firm*—Fei-Fei Chao; Andrews Kurth, LLP

(57) ABSTRACT

A method for synthesizing benzotriazole comprises acts of: preparing a first solvent comprising 2-(2-hydroxy-5-methylphenyl) benzotriazole, a basic agent and molecular sieves and a second solvent comprising 3-chloro-2-alkyl propylene; mixing the solvents; and heating the solvents. This method requires only one reaction vessel and produces few by-products, therefore is simpler and cheaper to produce. Furthermore, the molecular sieves are cheaper than catalysts in conventional reactions and may be recycled, giving even greater economic benefits.

14 Claims, 1 Drawing Sheet ature, which is between 180° C. and 250° C., to allow a Claisen rearrangement to occur. Then, in act (e), the molecular sieves, which are insoluble in the organic solvents are filtered out. In act (f), the recrystallizing is performed with a third organic solvent. The third organic solvent may be, but is not limited to, methanol.

METHOD FOR SYNTHESIZING BENZOTRIAZOLE

BACKGROUND OF THE INVENTION

1. Field of the Invention

The present invention relates to a method for synthesizing benzotriazole in a one-pot reaction that does not require isolation of intermediates or a precious metal catalyst.

2. Description of the Prior Arts

Benzotriazole is frequently used in cosmetics and sunscreens or the like to absorb ultraviolet (UV) light and prevent harmful effects of UV light.

Benzotriazole absorbs UV, especially at wavelengths of 280 nm and 320 nm in the UV-B range and 320 nm and 400 nm of the UV-A range. Therefore, simple and efficient synthesis routes of benzotriazole are much desired. Prior patents U.S. Pat. Nos. 3,715,334, 3,947,436, 4,051,161, 4,122,233, 4,188,451, 4,233,430, 4,316,033, 4,342,742, 4,373,060, 4,457,911, 4,489,057, 4,490,356, 4,696,969, 4,814,162, 4,851,587, 4,859,759, 4,868,251, 5,089,250, EP 0,138,321, EP 0,354,145 and GB 2,077,280 disclosed several methods for preparing benzotriazole. These methods use 2-(2-hydroxy-5-methylphenyl) benzotriazole or its derivatives as a reactant to react with chloroalkyl propylene in a basic organic solvent at high temperature through a Claisen rearrangement. However, the Claisen rearrangement creates many by-products. Therefore, these methods must include a separation step to remove a desired benzotriazole product and therefore has the following drawbacks:

1. Polar organic solvents that easily bring water are used in the reaction. However, water proceeds through a different reaction path and competes with the desired reaction raising an amount of undesired by-products. Therefore, the separation step is further complicated and slowed.

2. Low reaction yields.

3. A rate of reaction is higher between 180° C. and 250° C.

4. After forming an initial intermediate, these methods require a separation step to separate by-products from the intermediate before proceeding to a Claisen rearrangement, therefore, requiring multiple steps and reaction vessels.

5. Purification requires large amounts of organic solvents that require expensive disposal and pollute the environment.

6. These methods require a metal catalyst, frequently particles of a metal catalyst that require a large investment for procurement. The metal catalyst is not easily separated from the solvent, and any that remains causes greater environmental damage if released and directly increases costs of the benzotriazole. The present invention has arisen to provide a method for synthesizing benzotriazole to overcome and obviate the drawbacks of the conventional methods.

SUMMARY OF THE INVENTION

The present invention provides methods for synthesizing benzotriazole, in particular, a method of synthesizing benzotriazole in a one-pot reaction that does not require isolation of intermediates or a precious metal catalyst.

The method for synthesizing benzotriazole comprises acts of: preparing a first solvent comprising 2-(2-hydroxy-5-methylphenyl) benzotriazole, a basic agent and molecular sieves and a second solvent comprising 3-chloro-2-alkyl propylene; mixing the solvents; and heating the solvents This method requires only one reaction vessel and produces few by-products, therefore is simple and cheap. Furthermore, the molecular sieves are cheaper than metal catalysts in conventional reactions and may be recycled giving even greater economic benefits.

DETAILED DESCRIPTION OF THE PREFERRED EMBODIMENTS

Figure 1:
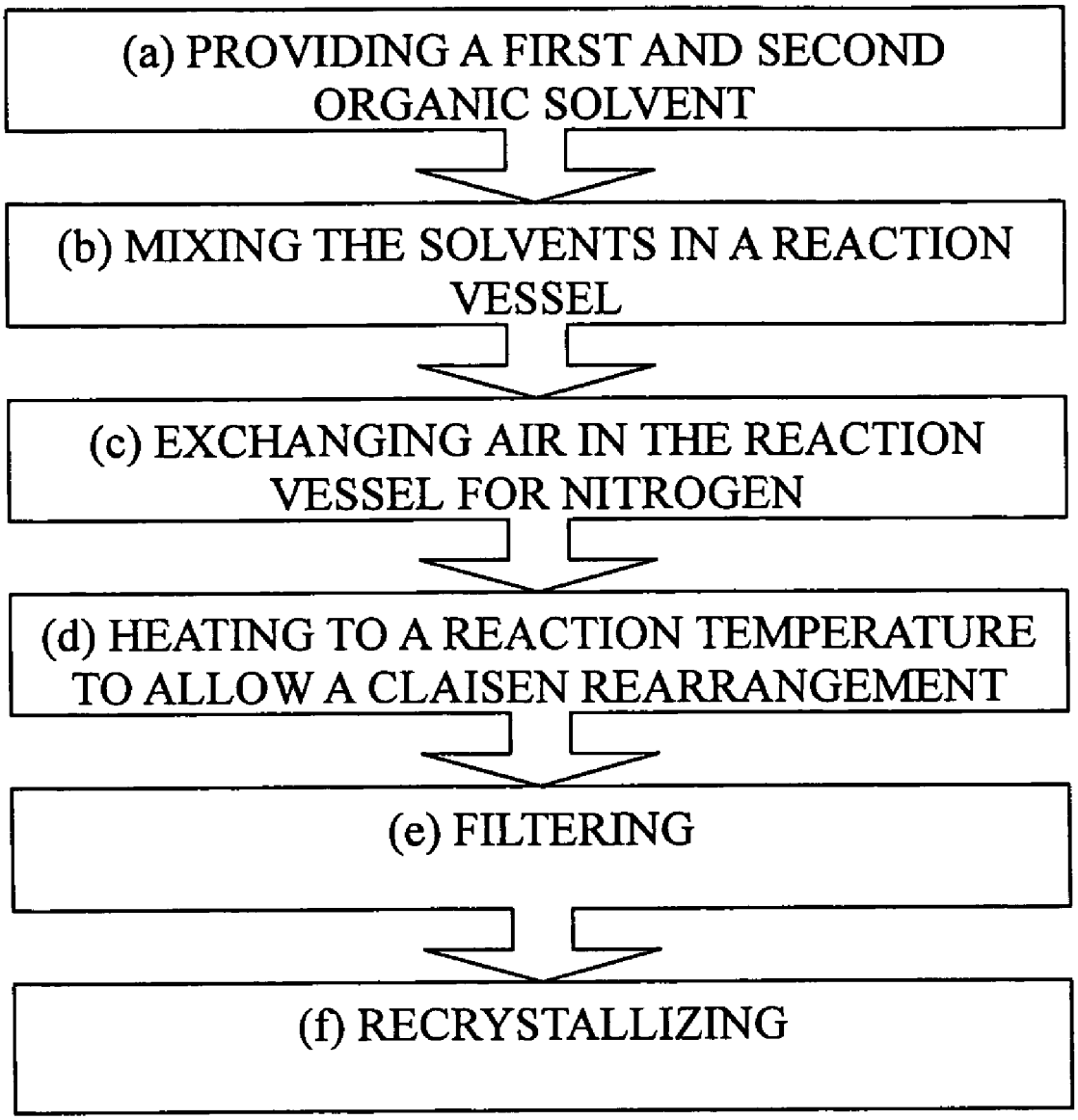
FIG. 1 is a flow diagram showing acts of a method for synthesizing benzotriazole in accordance with the present invention.

In describing and claiming the present invention, the following terminology will be used in according to the definitions as below.

As used herein, "molecular sieve" refers to a material containing small pores of a precise and uniform size, which is used as an adsorbent for gases or liquid.

As used herein, "recrystallization" refers to a kind of a purification process of solid. Different solvents can be used in the recrystallization depending upon different substances that have different solubilities in different solvents.

As used herein, "heating" refers to a kind of chemical step that let product of the chemical equation tend to thermodynamic equilibrium through Claisen rearrangement.

A method for synthesizing benzotriazole comprises acts of: (a) providing a first organic solvent and a second organic solvent. The first organic solvent comprises 2-(2-hydroxy-5-methylphenyl) benzotriazole, molecular sieves and a base. The second organic solvent comprises 3-chloro-2-alkyl propylene; (b) mixing the first and the second organic solvents in a reaction vessel; (c) exchanging air in the reaction vessel for nitrogen; (d) heating to a reaction temperature to allow a Claisen rearrangement; (e) filtering; and (f) recrystallizing. The method is represented by the following chemical equation:

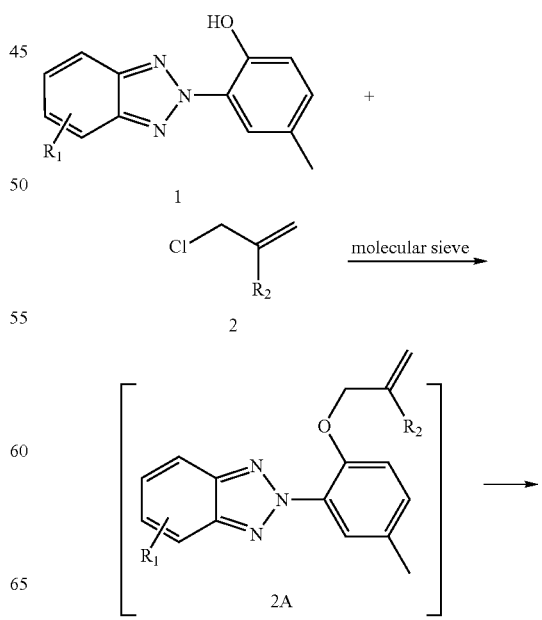

-continued

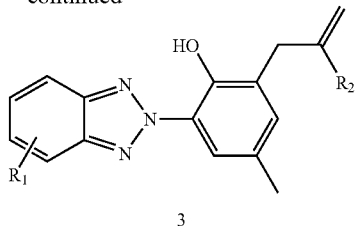

3

$R_1$ and $R_2$ groups are separately selected from the group consisting of hydrogen, benzyl, a one to eight carbon alkyl group, a one to four carbon alkoxy group and a one to four carbon siloxy group.

Preferably, 2-(2-hydroxy-5-methylphenyl) benzotriazole and 3-chloro-2-alkyl propylene are in a molar ratio between 1 to 2 and 1 to 4. Most preferably, the first organic solvent and the second organic solvent are in a ratio between 1 to 1 and 4 to 1. Preferably, 2-(2-hydroxy-5-methylphenyl) benzotriazole and the basic agent are in a ratio between 1 to 0.1 and 1 to 1.

The basic agent is an inorganic compound or an organic compound. Preferably, the inorganic compound is selected from the group consisting of sodium carbonate, potassium carbonate, sodium hydrogen carbonate and potassium hydrogen carbonate. Preferably, the organic compound is selected from the group consisting of triethylamine and tricaprylylamine.

Preferably, the molecular sieve has a pore size between 3 Å and 5 Å.

Preferably, the molecular sieve is calcium aluminum silicate.

Preferably, 2-(2-hydroxy-5-methylphenyl) benzotriazole and the calcium aluminum silicate are in the ratio between 1:0.3 and 1:3.0.

Preferably, the first organic solvent is N,N-dialkylaniline having alkyl groups containing between 1 and 3 carbon atoms. More preferably, the first organic solvent is N,N-dimethylaniline.

Preferably, the second organic solvent is alkyl ketone having an alkyl groups containing between 1 and 5 carbon atoms. More preferably, the second organic solvent is methyl ethyl ketone.

Preferably, the reaction temperature is between 70° C. and 190° C.

Preferably, recrystallizing is performed using a recrystallization solvent that is selected from the group comprising methylene halide, N,N-dimethylformamide, alcohol of the alkyl group containing 1 to 5 carbon atoms and halobenzene.

The following examples illustrate and exemplify the present invention; it should be understood that the examples and embodiments described herein are for illustrative purposes only and should not be construed as limiting the embodiments set forth herein.

EXAMPLE 1

Reaction with no Molecular Sieve 10 g of 2-(2-hydroxy-5-methylphenyl) benzotriazole (0.044 moles), 4.5 g of the triethylamine (0.044 moles) and 16.1 g of N,N-dimethylaniline (0.13 moles) were introduced into a reacting chamber and stirred for 5 minutes to make a solution. 0.09 moles of 3-chloro-2-alkyl propylene were dissolved in the methyl ethyl ketone and then were added to the solution within 10 minutes into the reacting chamber where air inside the chamber was nitrogen gas. The solution was heated to 80° C. for 5 hours, further heated to 180° C. and held on for 3 hours to allow Claisen rearrangement before removing heat and allowing to cool to 80° C. Then, the solution was filtered using activated carbon A filtrate was recrystallized using 40 ml of isopropanol. Then, filter paper was used to filter a yellow recrystallized filtrate. The yellow recrystallized filtrate was isolated by column chromatography to obtain 3.1 g of 2-(2-hydroxyl-5-methylphenyl) benzotriazole, 0.2 g of 2-(5-methyl-2-(2-methyl-propenyloxy)-phenyl)-2H-benzotriazole, 4.9 g of 1-methallyl-2-(2'-hydroxyl-5'-methylphenyl) benzotriazole (yield: 40%) and 0.1 g of by-products including 2-benzotriazol-2-4 methyl-6-(2-methyl-propenyl)-phenol.

EXAMPLE 2

Reaction with 3 Å Molecular Sieve 10 g of 2-(2-hydroxy-5-methylphenyl) benzotriazole (0.044 moles), 4.5 g of the triethylamine (0.044 moles), 16.1 g of N,N-dimethylaniline (0.13 moles) and 16 g of 3 Å molecular sieves (that are UOP type 3 Å beads purchased from the Fluka company) were introduced into a reacting chamber and stirred for 5 minutes to form a solution. 0.09 moles of 3-chloro-2-alkyl propylene was dissolved in methyl ethyl ketone and added to the solution within 10 minutes into the reacting chamber where air inside the reaction chamber was nitrogen. Then, the solution was heated to 80° C. for 5 hours and monitored using HPLC until reaction was complete and further heated to 180° C. and held on for 3 hours to allow the Claisen rearrangement before being left to cool to 80° C. The solution was was filtered using activated carbon. A filtrate was recrystallized using 40 ml of isopropanol. Then, filter paper was used to filter a white recrystallized filtrate being. 8.9 g of 1-methallyl-2-(2'-hydroxyl-5'-methylphenyl) benzotriazole remained on the filter paper (yield: 72%, purity: 99.1%, melting point: 95° C.).

EXAMPLE 3

Reaction with 4 Å Molecular Sieve 10 g of 2-(2-hydroxy-5-methylphenyl) benzotriazole (0.044 moles), 4.5 g of the triethylamine (0.044 moles), 16.1 g of N,N-dimethylaniline (0.13 moles) and 16 g of 4 Å molecular sieves (that are UOP type 4 Å beads purchased from the Fluka company) were introduced into the reacting chamber and mixed to form a solution. 0.09 moles of 3-chloro-2-alkyl propylene was dissolved in methyl ethyl ketone and added to the solution within 10 minutes into the reacting chamber where air in the reacting chamber was nitrogen. Then, the solution was heated to 80° C. for 5 hours and a reaction completion was monitored using HPLC. Then, the solution was heated to 180° C. and held on for 3 hours to allow Claisen rearrangement and left to cool to 80° C. Then, the solution was filtered using active carbon. A filtrate was recrystallized using 40 ml of isopropanol. Then, filter paper was used to filter a white recrystallized filtrate being 10.7 g of 1-methallyl-2-(2'-hydroxyl-5'-methylphenyl) benzotriazole (yield: 86%, purity: 99.9%, melting point: 95° C.).

EXAMPLE 4

Reaction with 5 Å Molecular Sieve 10 g of 2-(2-hydroxy-5-methylphenyl) benzotriazole (0.044 moles), 4.5 g of the triethylamine (0.044 moles), 16.1 g of N,N-dimethylaniline (0.13 moles) and 16 g of 5 Å molecular sieves (that are UOP type 4 Å beads purchased from the Fluka company) were introduced into the reacting chamber and mixed to form a solution. 0.09 moles of the 3-chloro-2-alkyl propylene was dissolved in the methyl ethyl ketone and added to the solution within 10 minutes into the reacting chamber where air in the reacting chamber was nitrogen. Then, the solution was heated to 80° C. and for 5 hours and monitored using HPLC. Then, the solution was further heated to 180° C. and held on for 3 hours to allow a Claisen rearrangement and cooled to 80° C., before being filtered using active carbon. A filtrate was recrystallized in 40 ml of isopropanol. Then, filter paper was used to filter a a white recrystallization filtrate being 10 g of 1-methallyl-2-(2'-hydroxyl-5'-methylphenyl) benzotriazole (yield: 81%, purity: 99.6%, melting point: 95° C.).

TABLE 1

Table showing pore size of above the foregoing experiments, yield, product by weight and purity.

| Pore size | Ex 1 - None | Ex 2 - 3 Å | Ex 3 - 4 Å | Ex 4 - 5 Å |
|---|---|---|---|---|
| Product (g) | 4.9 | 8.9 | 10.7 | 10 |
| Yield (%) | 40 | 72 | 86 | 81 |
| Purity (%) | — | 99.1 | 99.9 | 96 |

According to the examples and experimental data, the method for synthesizing benzotriazole can synthesize benzotriazole requires no separation stage, so is a one pot operation. Therefore, operational procedures are simplified reducing time expended and greatly enhancing production yields thereby reducing product costs. Additionally, molecular sieves can be recycled and require lower initial investment than conventional methods, further reducing costs significantly.

Even though numerous characteristics and advantages of the present invention have been set forth in the foregoing description, together with details of the structure and function of the invention, the disclosure is illustrative only. Changes may be made in detail, especially in matters of shape, size and arrangement of parts within the principles of the invention to the full extent indicated by the broad general meaning of the terms in which the appended claims are expressed.

What is claimed is:

1. A method for synthesizing benzotriazole having formula 3 comprising the steps of:

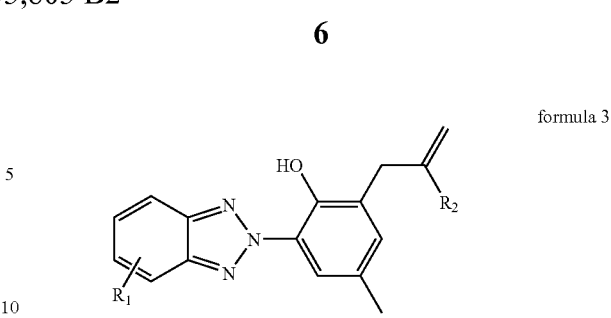

formula 3

(a) providing
a first organic solvent comprising formula 1;

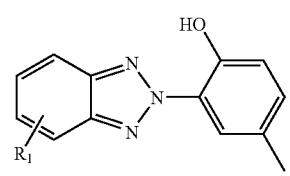

formula 1 a molecular sieve;
a basic agent; and
a second organic solvent comprising formula 2

formula 2

(b) mixing the first and the second organic solvents in a reaction vessel;
(c) exchanging air in the reaction vessel for nitrogen;
(d) heating to a reaction temperature to allow a Claisen rearrangement with the following chemical equation:

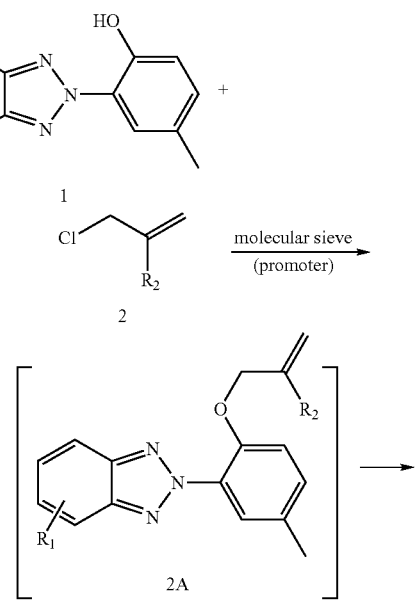

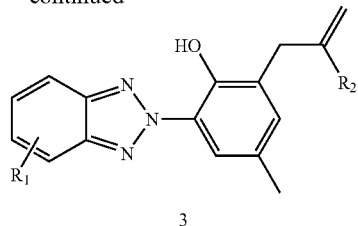

(e) obtaining a product containing formula 3,
wherein $R_1$ and $R_2$ are separately selected from the group consisting of hydrogen, benzyl, one to eight carbon alkyl group, one to four carbon alkoxy group and one to four carbon siloxy group.

2. The method as claimed in claim 1, further comprising acts of:
(f) filtering the product containing formula 3 after the Claisen rearrangement to obtain a filtered product containing formula 3; and
(g) recrystallizing the filtered product containing formula 3 to obtain formula 3.

3. The method as claimed in claim 2, wherein the molecular sieves have a pore size between 3 Å to 5 Å.

4. The method as claimed in claim 3, wherein the molecular sieves are calcium aluminum silicates.

5. The method as claimed in claim 4, wherein formula 1 and the calcium aluminum silicates in the ratio are between 1:0.3 and 1:3.0.

6. The method as claimed in claim 1, wherein the basic agent is an inorganic compound that is selected from the group consisting of sodium carbonate, potassium carbonate, sodium hydrogen carbonate and potassium hydrogen carbonate.

7. The method as claimed in claim 1, wherein the basic agent is an organic compound that is selected from the group consisting of triethylamine and tricaprylylamine.

8. The method as claimed in claim 2, wherein the first organic solvent is N,N-dialkylaniline having an alkyl group containing 1 to 3 carbon atoms.

9. The method as claimed in claim 8, wherein the first organic solvent is N,N-dimethylaniline.

10. The method as claimed in claim 1, wherein the second organic solvent is alkyl ketone having an alkyl group containing between 1 and 5 carbon atoms.

11. The method as claimed in claim 10, wherein the second organic solvent is methyl ethyl ketone.

12. The method as claimed in claim 1, wherein the first organic solvent and the second organic solvent are in a ratio between 1 to 1 and 4 to 1.

13. The method as claimed in claim 2, wherein recrystallizing the filtered product containing formula 3 is using a recrystallization solvent that is selected from the group consisting of methylene halide, N,N-dimethylformamide, alcohol of the alkyl group containing 1 to 5 carbon atoms and halobenzene.

14. The method as claimed in claim 2, wherein the reaction temperature is between 70° C. and 190° C.

* * * * *